United States Patent [19]
Fox et al.

[11] Patent Number: 5,437,628
[45] Date of Patent: Aug. 1, 1995

[54] CURVED TAMPON APPLICATOR HAVING AN IMPROVED FINGERGRIP

[75] Inventors: Donald G. Fox, Neenah; Daniel J. Heuer, Larsen; Laurie Couture-Dorschner, Greenville; Mary S. Semanek, Neenah, all of Wis.

[73] Assignee: Kimberly-Clark Corporation, Neenah, Wis.

[21] Appl. No.: 150,678

[22] Filed: Nov. 10, 1993

[51] Int. Cl.⁶ ............................................. A61F 13/28
[52] U.S. Cl. ........................................ 604/14; 604/1; 604/11; 604/13; 604/15; 604/904
[58] Field of Search ........................... 604/11–18, 604/904, 1–3

[56] References Cited

U.S. PATENT DOCUMENTS

| | | |
|---|---|---|
| 1,224,735 | 5/1917 | Gamache, Jr. et al. . |
| 2,386,590 | 10/1945 | Calhoun . |
| 2,587,717 | 3/1952 | Fourness . |
| 2,879,770 | 3/1959 | Graham, Jr. . |
| 3,042,040 | 7/1962 | Galik . |
| 3,059,642 | 10/1962 | Gershen . |
| 3,063,453 | 11/1962 | Brecht . |
| 3,068,867 | 12/1962 | Bletzinger et al. . |
| 3,086,527 | 4/1963 | Forrest . |
| 3,090,385 | 5/1963 | Brecht . |
| 3,103,929 | 9/1963 | Brecht . |
| 3,124,134 | 3/1964 | Gardner . |
| 3,351,060 | 11/1967 | De Woskin . |
| 3,409,011 | 11/1968 | Mittag . |
| 3,429,312 | 2/1969 | Stump . |
| 3,575,169 | 4/1971 | Voss . |
| 3,643,661 | 2/1972 | Crockford . |
| 3,645,263 | 2/1972 | Bates . |
| 3,762,413 | 10/1973 | Hanke . |
| 3,765,417 | 10/1973 | Crockford . |
| 3,799,165 | 3/1974 | Wennerblom et al. . |
| 3,805,786 | 4/1974 | Bernardin et al. . |
| 3,807,399 | 4/1974 | Morman et al. . |
| 3,831,605 | 8/1974 | Fournier ............................ 604/17 |
| 3,835,856 | 9/1974 | Warncke . |

| | | |
|---|---|---|
| 5,087,239 | 2/1992 | Beastall et al. . |
| 5,158,535 | 10/1992 | Paul et al. . |

(List continued on next page.)

FOREIGN PATENT DOCUMENTS

| | | |
|---|---|---|
| 121844 | 8/1946 | Australia . |
| 700840 | 12/1964 | Canada . |
| 7707411 | 12/1977 | South Africa . |
| 2166656A | 5/1986 | United Kingdom . |

*Primary Examiner*—Randall L. Green
*Assistant Examiner*—P. Zuttarelli
*Attorney, Agent, or Firm*—Thomas J. Connelly

[57] ABSTRACT

A curved tampon applicator is disclosed having an improved fingergrip for preventing rotation of the applicator during insertion of a catamenial tampon into a woman's vagina. The applicator includes a tubular member having an arcuate shape with a centerline formed on an arc having a predetermined radius of curvature. The tubular member has a stepped outer profile with an enlarged portion designed to house a tampon joined to a smaller fingergrip portion. The tubular member has a forward end through which the tampon is ejected and a rearward end through which a plunger is slidable. The fingergrip portion has a passageway formed therethrough which is sized and configured to receive the plunger and an exterior periphery. Formed on the exterior periphery of the fingergrip portion are first and second pairs of flat surfaces. The first pair of the flat surfaces is aligned parallel to a plane coincident with a radius forming the arcuate centerline of the tubular member and the second pair of flat surfaces is aligned perpendicular to the first pair of flat surfaces. The fingergrip portion also contains a plurality of spaced apart ribs, each of which completely surrounds the exterior periphery. The ribs cooperate with the first and second pairs of flat surfaces to prevent rotation of the curved tampon applicator during insertion of a tampon into a woman's vagina.

21 Claims, 3 Drawing Sheets

U.S. PATENT DOCUMENTS

| | | |
|---|---|---|
| 3,895,634 | 7/1975 | Berger et al. . |
| 4,269,187 | 5/1981 | Sakurai et al. . |
| 4,276,881 | 7/1981 | Lilaonitkul . |
| 4,318,405 | 3/1982 | Sneider . |
| 4,332,251 | 6/1982 | Thompson . |
| 4,361,150 | 11/1982 | Voss . |
| 4,411,647 | 10/1983 | Sakurai et al. . |
| 4,412,833 | 11/1983 | Wiegner et al. . |
| 4,424,054 | 1/1984 | Conn et al. . |
| 4,522,967 | 6/1985 | Sheldon et al. . |
| 4,536,178 | 8/1985 | Lichstein et al. . |
| 4,543,086 | 9/1985 | Johnson . |
| 4,573,963 | 3/1986 | Sheldon . |
| 4,676,773 | 6/1987 | Sheldon . |
| 4,857,044 | 8/1989 | Lennon . |
| 4,900,299 | 2/1990 | Webb . |
| 4,911,687 | 3/1990 | Stewart et al. . |
| 4,973,302 | 11/1990 | Armour et al. . |
| 5,061,274 | 10/1991 | Kensey . |
| 5,080,659 | 1/1992 | Nakanishi . |

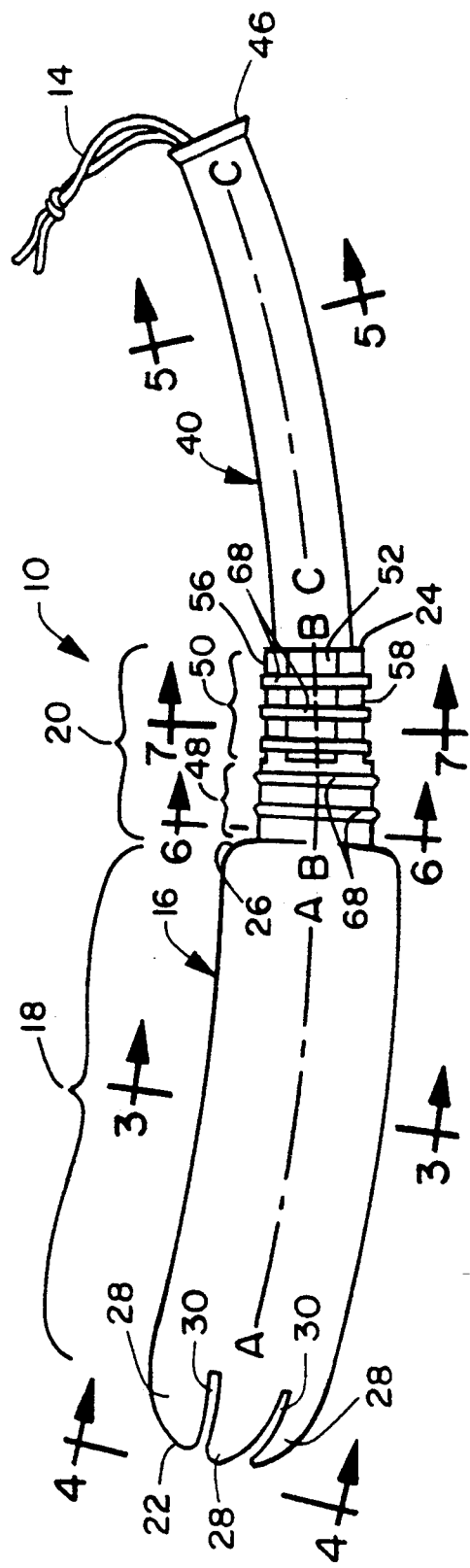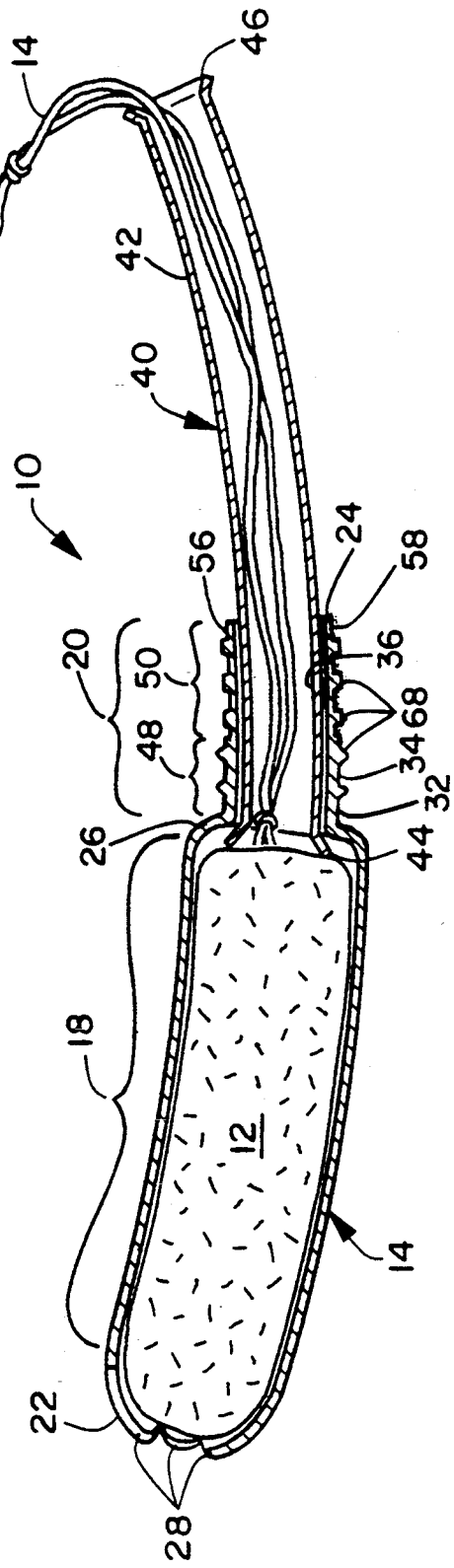

CURVED TAMPON APPLICATOR HAVING AN IMPROVED FINGERGRIP

FIELD OF THE INVENTION

This invention is related to a curved tampon applicator having an improved fingergrip portion for preventing the applicator from rotating during insertion of a catamenial tampon into a woman's vagina.

BACKGROUND OF THE INVENTION

Currently, catamenial tampons are manufactured so that they can be inserted into a woman's vagina in two different ways. One way is by digital insertion wherein a woman uses her fingers to position the tampon into her vagina. The second way is to insert the tampon with a tampon applicator wherein the tampon is assembled into an applicator during the manufacturing process. In use, the woman holds and operates the applicator in order to insert the tampon into her vagina. The use of an applicator to insert a tampon has surpassed the use of digital insertion primarily for sanitary reasons. Until now, most tampon applicators have been manufactured having a straight cylindrical profile which retains a straight cylindrically shaped tampon. A disadvantage of trying to insert a straight cylindrically shaped tampon with a straight applicator is that neither matches up with the arcuate profile of a woman's vaginal cavity. Therefore, some women experience discomfort when trying to insert a straight tampon using a straight applicator.

Curved tampon applicators have been designed and patented which are capable of housing arcuate shaped tampons so as to more closely approximate the curvature of a woman's vagina. These curved applicators with these curved tampons hold great promise for being more comfortable. However, one drawback over straight cylindrical tampon applicators has been recognized. With straight tampon applicators, rotation of the outer tube did not change the orientation of the tampon relative to the vaginal cavity. With a curved tampon applicator, if the outer tube is rotated during the insertion process, the tampon could be expelled such that instead of moving up into the vaginal cavity, the tampon is actually angled against the side wall of the vagina. Such action could cause discomfort or prevent easy insertion of the absorbent tampon into the woman's vagina.

In order to avoid rotation or twisting of the curved tampon applicator during the insertion process, an improved fingergrip portion has been developed which utilize two pairs of flat surfaces. The presence of two perpendicularly aligned pairs of flat surfaces serve to accommodate two of the more common styles used by women for holding an applicator.

Now a curved tampon applicator with an improved fingergrip portion has been invented which prevents the applicator from rotating during insertion of a catamenial tampon into a woman's vagina.

SUMMARY OF THE INVENTION

Briefly, this invention relates to a curved tampon applicator having an improved fingergrip portion for facilitating comfortable insertion of a catamenial tampon into a woman's vagina. The improved fingergrip prevents the curved tampon applicator from rotating during the insertion process. The applicator includes a tubular member having an arcuate shape with a centerline formed on an arc having a predetermined radius of curvature. The tubular member has a stepped outer profile with an enlarged portion designed to house a catamenial tampon joined to a smaller offset fingergrip portion. The tubular member has a forward end through which the tampon is ejected and a rearward end through which a plunger is slidable. The fingergrip portion has a unique exterior surface and a central passageway formed therethrough which is sized and configured to receive the plunger. Formed on the exterior surface of the fingergrip portion is a first pair of flat surfaces which are aligned parallel to a plane coincident with a radius forming the arcuate centerline of the tubular member and a second pair of flat surfaces aligned perpendicular to the first pair of flat surfaces. The fingergrip portion also contains a plurality of spaced apart ribs, each of which completely surrounds the exterior surface of the fingergrip portion. The ribs cooperate with the first and second pairs of flat surfaces to prevent the applicator from slipping or sliding between the woman's fingers during the insertion process.

The general object of this invention is to provide a curved tampon applicator having an improved fingergrip portion. A more specific object of this invention is to provide a curved tampon applicator having a fingergrip portion which prevents rotation of the applicator during the insertion process.

Another object of this invention is to provide a curved tampon applicator having an improved fingergrip portion which include the first and second pairs of flat surfaces aligned in a unique orientation relative to the radius forming the arcuate centerline of the tubular member.

A further object of this invention is to provide a curved tampon applicator having an improved fingergrip portion which allows the user to hold the applicator in different ways.

Still another object of this invention is to provide a curved tampon applicator having an improved fingergrip portion which contains a plurality of spaced apart ribs which prevent the applicator from slipping or sliding between a user's fingers.

Still further, an object of this invention is to provide a curved tampon applicator having an improved fingergrip portion which can easily be handled with one hand.

Other objects and advantages of the present invention will become more apparent to those skilled in the art in view of the following description and the accompanying drawings.

BRIEF DESCRIPTION OF THE DRAWINGS

FIG. 1 is a side elevation view of a curved tampon applicator having an improved fingergrip portion for facilitating insertion of a catamenial tampon into a woman's vagina.

FIG. 2 is a cross-sectional view of the curved tampon applicator shown in FIG. 1 depicting a catamenial tampon housed in the outer tube.

DETAILED DESCRIPTION OF THE PREFERRED EMBODIMENT

Referring to FIGS. 1 and 2, a curved tampon applicator 10 is shown containing a catamenial tampon 12. The catamenial tampon 12 is intended to be inserted into a woman's vagina during her menstrual period to block the flow of menstrual fluid, blood, body tissue, etc. therefrom. A withdrawal string 14 is attached to one end of the absorbent tampon 12 and functions to provide a means for removing the tampon 12 from the woman's vagina after it has absorbed a certain quantity of body fluid.

The curved tampon applicator 10 can consist of one or more telescopically operable members. For purposes of discussion, the curved tampon applicator 10 will be described as a two piece assembly. The curved applicator 10 can be formed from a thermoplastic material or blends thereof, which can be injection molded or extrusion molded. Alternatively, the curved tampon applicator 10 can be constructed out of one or more layers of paper or cardboard. If possible, the material used should be water dispersible, water soluble, photodegradable or biodegradable so as to be environmentally friendly.

The curved applicator 10 includes a tubular member 16, which is also referred to as an outer tube. The tubular member 16 has an arcuate shape with a centerline A—A formed on an arc with a predetermined radius of curvature. The arc can be formed with a radius of curvature of between about 6 to 10 inches (about 152.4 to 254 millimeters), preferably between about 7 to 9 inches (about 177.8 to 228.6 mm), and most preferably, about 8 inches (about 203.2 mm). An arc having a certain radius of curvature is equivalent to an arcuate segment of a circle having a given radius. U.S. Pat. No. 5,158,535 teaches a curved tampon applicator and is incorporated by reference and made a part hereof.

Figure 3:
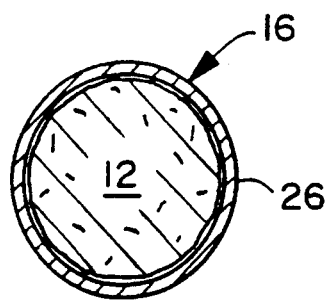
FIG. 3 is a cross-sectional view of the tubular member taken along line 3—3 of FIG. 1.
Figure 4:
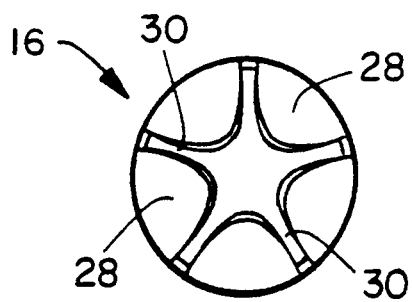
FIG. 4 is an end view of the tubular member taken along line 4—4 of FIG. 1.

The tubular member 16 is a hollow tube having an overall length of about 2 to 3 inches (about 50.8 to 76.2 mm) and a diameter of about ¼ to ¾ of an inch (about 6.35 to 19.05 mm). Preferably, the tubular member 16 is made from a low density polyethylene. The tubular member 16 has a stepped outer profile with an enlarged portion 18 joined to a smaller fingergrip portion 20. The tubular member 16 contains a forward end 22 spaced apart from a rearward end 24. The enlarged portion 18 is designed to house an absorbent tampon 12 and has a generally circular or round cross-sectional profile, as is shown in FIG. 3. The enlarged portion 18 has an internal diameter which is sized to be slightly larger than the outside diameter of the absorbent tampon 12. The enlarged portion 18 has a wall 26 which tapers in thickness as it approaches the forward end 22. The taper is beneficial in that it permits a plurality of petals 28, see FIG. 4, to be formed approximate the forward end 22. The petals 28 are thin, flexible members separated by slots or grooves 30. The petals 28 are capable of bending radially outward as the absorbent tampon 12 is expelled from the curved tampon applicator 10. An odd number of petals 28, such as 3, 5, etc. should be utilized instead of an even number of petals 28 because an odd number of petals 28 will prevent the enlarged portion 18 from collapsing or flattening after the tampon 12 has been expelled. By preventing such collapse, one can be assured that vaginal tissue will not be pinched. This will assure safe use of the curved applicator 10 and could contribute to additional sales.

The fingergrip portion 20 is a hollow member having a wall 32 which can vary in thickness from between about 0.5 to 1.5 mm. The fingergrip portion 20 has a length measured along the centerline of said tubular member 16 of between about ½ to 1 inch (about 12.7 to 25.4 mm), preferably about ⅝ of an inch (about 15.8 mm). The fingergrip portion 20 has an exterior periphery 34 and an internal periphery 36. The exterior periphery 34 varies in cross-section along the length of the fingergrip portion 20 while the interior periphery 36 has a constant elliptical or oval-shaped configuration. The interior periphery 36 forms a passageway 38 which extends through the fingergrip portion 20 along a centerline B—B and opens into the interior of the enlarged portion 16. The passageway 38 is sized and configured to receive a plunger 40, which is also commonly referred to as an inner tube.

Figure 5:
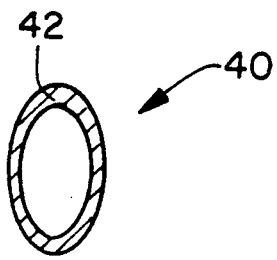
FIG. 5 is a cross-sectional view of the plunger taken along line 5—5 of FIG. 1.
Figure 6:
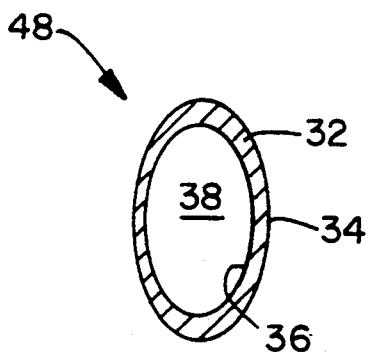
FIG. 6 is a cross-sectional view of the fingergrip portion taken along line 6—6 of FIG. 1.

Referring to FIG. 5, the plunger 40 is shown as a hollow, elliptical or oval-shaped member having a uniform thin wall 42. However, it should be noted that the plunger 40 can be a solid member, such as a cardboard stick if desired. For purposes of discussion, the plunger 40 will be described as a tubular member. The thin wall 42 can have a thickness ranging from about 0.01 to 0.02 inches (about 0.25 to 0.50 mm). The wall 32 of the fingergrip portion 20 is generally thicker than the wall 42 of the plunger 40 because it has to provide structural support for the plunger 40. The plunger 40 can be formed from a thermoplastic material, such as high density polyethylene. The thermoplastic material should be capable of being injection molded. Alternatively, the plunger 40 can be constructed from one or more layers of paper or cardboard. The plunger 40 has an arcuate shape with a centerline C—C formed on an arc having a predetermined degree of curvature. The exterior periphery of the plunger 40 is sized and configured to mate with and be slidable within the passageway 38. The oval-shaped configuration of both the plunger 40 and the passageway 38 allow the plunger 40 and the tubular member 16 to move in a telescoping fashion while preventing the plunger 40 from rotating within the fingergrip portion 20. This is important because the plunger 40 is designed to push the absorbent tampon 12 out of the forward end 22 of the enlarged portion 18. If rotation could occur, the plunger 40 could bind up in the fingergrip portion 20 or rub against the inner periphery of the wall 26 of the enlarged portion 18 and removal of the tampon 12 could be hindered.

The plunger 40 also has first and second spaced apart ends 44 and 46, respectively. At least one, and preferably both of the ends 44 and 46 are flared after the plunger 40 has been inserted into the tubular member 16. The flaring assures that once assembled, the plunger 40 will not separate from the tubular member 16. The amount of flare can vary depending upon the dimensions of the plunger 40 and the tubular member 16, as well as the diameter of the tampon 12 which is to be ejected. For ease of manufacture, the plunger 40 should be slightly longer in length than the length of the tubular member 16. This difference in length will facilitate flaring the ends 44 and 46 after the plunger 40 has been assembled in the tubular member 16 and will also provide assurance that the plunger 40 has sufficient length to expel the tampon 12 from the tubular member 16. The plunger 40 is designed to push the tampon 12 out through the forward end 22 of the enlarged portion 18.

When the consumer purchases the curved tampon applicator 10, the tampon 12 is housed in the enlarged portion 18 and the plunger 40 is extending out of the fingergrip portion 20, as shown in FIG. 1. When the woman wishes to insert the tampon 12, she positions the tubular member 16 in her vagina and depresses the plunger 40. This causes the first end 44 of the plunger 40 to contact an end of the tampon 12 and pushes it forward. As the tampon 12 is pushed forward, it causes the petals 28 to radially spread apart and form an opening through which the tampon 12 can be released from the tubular member 16. The woman will continue to depress the plunger 40 in a steady fashion until the tampon 12 is completely ejected from the curved tampon applicator 10.

Referring again to FIG. 1, the fingergrip portion 20 is formed on the centerline B—B which is shown coaxially aligned with the centerline A—A of the enlarged portion 18. The radius of curvature of the centerline B—B could be different from the radius of curvature of the centerline A—A. Preferably, the radius of curvature of the fingergrip portion 20 will be approximately equal to the radius of curvature of the plunger 40. It should be noted that the fingergrip portion 20 could have a radius of curvature which is slightly smaller or larger than the radius of curvature of the plunger 40 if desired.

The fingergrip portion 20 can be offset toward the longer surface of the enlarged portion 18. By "longer surface" is meant the lower half of the wall shown in FIG. 2. An offset provides better control for the user when she inserts the enlarged portion 18 into her vagina. The combination of the offset and the greater degree of curvature produces a curved tampon applicator 10 which is easier to handle. The offset also enables the curved tampon applicator 10 to have more of an arcuate shape without the need of increasing the degree of curvature of the enlarged portion 18. It has been found that when the degree of curvature of the enlarged portion 18 is increased, for example, when the radius of curvature is formed with a smaller radius, the comfort level will decrease. Furthermore, when the radius of curvature of the enlarged portion 18 is less than about 6 inches (about 152.4 millimeters), the petals 28 can cause pinching or scratching of the vaginal tissue either during insertion or removal of the applicator 10.

It should be noted that the offset of the fingergrip portion 20 gives the curved tampon applicator 10 the appearance of having a greater degree of curvature while utilizing a very gentle curvature for the enlarged portion 18. This combination further aids in the aesthetic appearance and visual perception of the curved tampon applicator 10.

Figure 7:
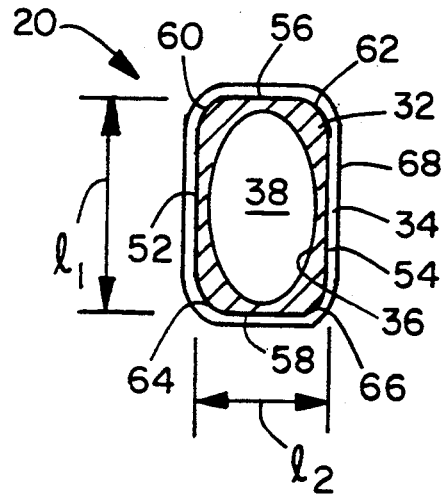
FIG. 7 is a cross-sectional view of the fingergrip portion taken along line 7—7 of FIG. 1.

The fingergrip portion 20 structurally contains a first, relatively short, exterior section 48 which has an oval cross-sectional shape. The first section 48 is situated adjacent to the enlarged portion 18. The first section 48 can be about ⅛ to ⅜ of an inch (about 3.2 to 9.5 mm.) in length. Formed adjacent to the first section 48 is a second, generally longer, exterior section 50. The second section 50 has a generally rectangular cross-sectional configuration, as best shown in FIG. 7. Formed on the second section 50 is a first pair of flat surfaces 52 and 54 and a second pair of flat surfaces 56 and 58. The first and second pairs of flat surfaces 52 and 54, and 56 and 58, respectively, change the exterior periphery 34 of the fingergrip portion 20. The first and second pairs of flat surfaces 52 and 54, and 56 and 58, can span a length, as measured along the longitudinal centerline B—B, of between about 5 to 20 mm, preferably between about 8 to 15 mm. Another way of stating this is to say that the first and second pairs of flat surfaces 52 and 54, and 56 and 58, respectively, extend the full length of the second section 50. For best results, the first and second pairs of flat surfaces 52 and 54, and 56 and 58, respectively, should extend more than one half of the total length of the fingergrip portion 20, measured along the arcuate centerline, starting from the rearward end 24.

Referring to FIG. 7, each of the first pair of flat surfaces 52 and 54 has a length $l_1$ of between about 4 to 5 mm, preferably about 4.5 mm. The first pair of flat surfaces 52 and 54 are aligned approximately parallel to one another and both are aligned parallel to a plane coincident with a radius forming the arcuate centerline of the enlarged portion 18. The thickness of the wall 32 of the fingergrip portion 20 at the first pair of flat surfaces 52 and 54 can range between about 0.6 to 0.7 mm, preferably about 0.63 mm. Each of the second pair of flat surfaces 56 and 58 has a length $l_2$ of about 3 to 4 mm, preferably about 3.5 mm. The second pair of flat surfaces 56 and 58 are aligned approximately parallel to one another and both are aligned approximately perpendicular to the first pair of flat surfaces 52 and 54. The thickness of the wall 32 of the fingergrip portion 20 at the second pair of flat surfaces 56 and 58 can be equal to the wall thickness of the first pair of flat surfaces 52 and 54. A suitable wall thickness for the second pair of flat surfaces 56 and 58 is between about 0.6 to 0.7 mm, preferably about 0.64 mm. The length $l_2$ of the second pair of flat surfaces 56 and 58 is less than or shorter than the length $l_1$ of the first pair of flat surfaces 52 and 54. One reason for this is that the first pair of flat surfaces 52 and 54 are arranged to be the primary surfaces which will be contacted by the user's fingertips. Therefore, they are slightly larger to provide more contact area. Another reason is that the oval-shaped interior periphery 36 of the fingergrip portion 20 is configured to receive the oval-shaped plunger 40. Since the oval shape has a greater height than width, it only makes sense that the length dimension of the first pair of flat surfaces 52 and 54 will be greater than the length dimension of the second pair of flat surfaces 56 and 58.

Bridging the first and second pairs of flat surfaces 52 and 54, and 56 and 58, respectively, are four rounded corners 60, 62, 64 and 66. The rounded corners 60, 62, 64 and 66 have a wall with a greater thickness than either the first or second pairs of flat surfaces 52 and 54, and 56 and 58, respectively. The reason for this is that the rounded corners 60, 62, 64 and 66 provide the structural integrity to the fingergrip portion 20 and prevent the interior periphery 36 from being distorted when the user squeezes the fingergrip portion 20 during the insertion process. The rounded corners 60, 62, 64 and 66 can have a thickness ranging from about 0.5 to 1.2 mm, preferably about 1.0 mm.

A plurality of spaced apart ribs or protrusions 68 are formed about the exterior periphery 34 of the fingergrip portion 20. The ribs 68 extend beyond the exterior periphery 34 by about 0.2 mm to about 0.5 mm, preferably about 0.4 mm. The ribs 68 completely surround the exterior periphery 34 to form a closed ring or loop. By a "closed ring or loop" is meant a ring or loop spanning or covering 360° with no breaks therein. The ribs 68 can be uniformly arranged as shown in FIG. 1 or they can be situated at various distances from one another. Alternatively, the ribs 68 can be arranged in groups or clusters. A spacing of about 1 to 5 mm is satisfactory for most tampon applicators. The ribs 68 preferably are arranged parallel to one another. The number of ribs 68 can vary depending upon the size of the fingergrip portion 20, the spacing between the ribs 68, the material from which the curved tampon applicator 10 is made, etc. For good results, three to ten ribs 68 are satisfactory. Preferably, four to eight ribs 68 are present, with five ribs 68 being most preferred. The ribs 68 cooperate with the first and second pairs of flat surfaces 52 and 54, and 56 and 58, respectively, to prevent the user's fingers from sliding or slipping off the flat surfaces 52, 54, 56 and 58. When the user's fingers are maintained in their desired position, the curved tampon applicator 10 can be utilized without the fear that it will rotate or twist during the insertion process.

One of the primary differences of the present curved tampon applicator 10 over the prior art is that the prior art has not utilized two pairs of differently sized flat surfaces in combination with an oval shaped section, all of which are surrounded by radially extending ribs 68. Furthermore, on straight cylindrically shaped tampon applicators, rotation or twisting is not a problem since such rotation does not change the orientation of the applicator relative to the vaginal opening. In the present invention, the ribs 68 cooperate with both the first and second pairs of flat surfaces 52 and 54, and 56 and 58, respectively, to prevent slippage while adding flexibility in the manner in which the curved tampon applicator 10 can be held. The usefulness of the improved fingergrip portion 20 will be explained below in reference to FIG. 8.

Figure 8:
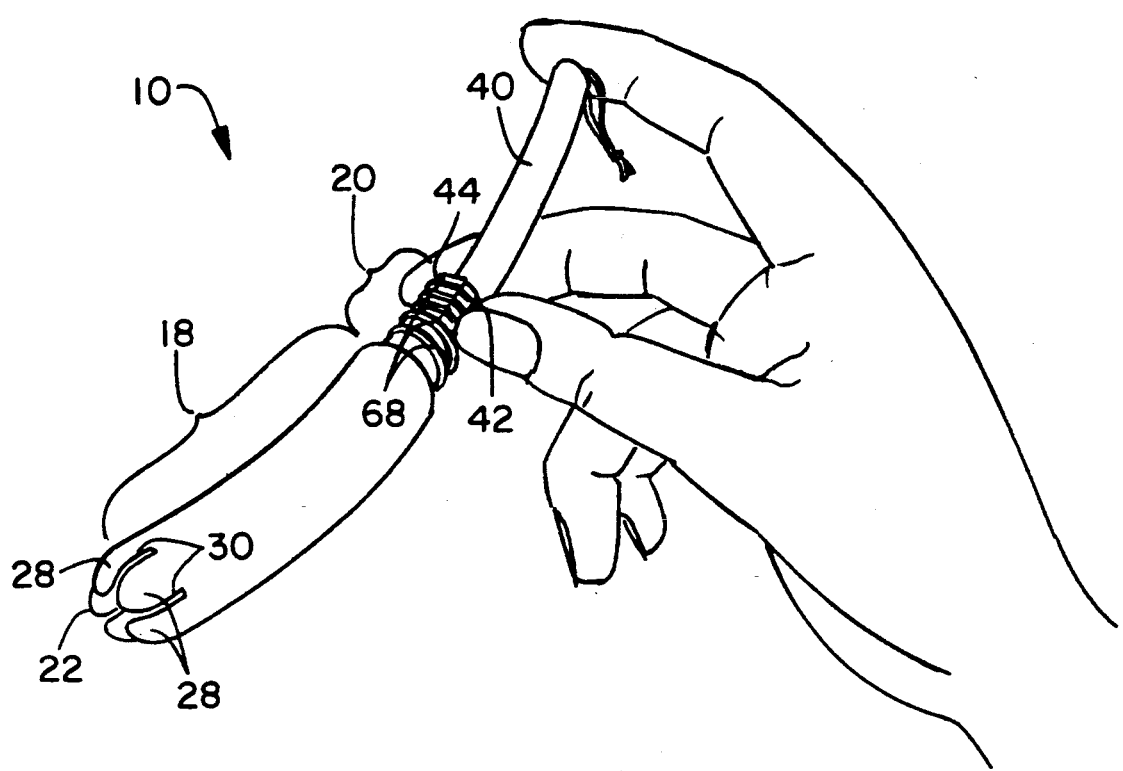
FIG. 8 is a schematic view of a woman's hand holding the curved tampon applicator of FIG. 1 in one commonly accepted position.

Referring to FIG. 8, the curved tampon applicator 10 is shown being held in the hand of a woman in the most commonly accepted fashion. In this position, the thumb and middle finger are positioned on the first pair of flat surfaces 52 and 54, respectively, and the index finger is positioned on the second end 46 of the plunger 40. In this particular arrangement, the flat surfaces 52 and 54, which are wider than the second pair of flat surfaces 56 and 58, provide two comfortable surfaces which fit the tips of the user's thumb and middle finger. However, for those women who feel that it is more comfortable to hold the curved applicator at a 90° orientation, they can place their thumb and middle finger on the second pair of flat surfaces 56 and 58. The length $l_2$ of the second pair of flat surfaces 56 and 58 is not as great as that of the first pair of flat surfaces 52 and 54 but still provide sufficient gripping area for the tips of the user's thumb and the middle finger. Women will no longer be required to hold the applicator in only one manner. This may seem like a trivial matter but for women who suffer from arthritis, joint inflammation, partial or complete hand or finger paralysis, hand deformity or other type of medical impairment, such an improved fingergrip is welcome.

Referring again to FIG. 1, one will notice that five ribs 68 are present. Two of the ribs 68 surround the first section 48 and have a circular cross-sectional configuration. The remaining three of the ribs 68 surround the second section 50 and have a generally rectangular cross-sectional configuration. This arrangement, wherein a majority of the ribs 68 are situated on the flat surfaces 52, 54, 56 and 58 allows the curved tampon applicator 10 to be used without encountering rotation and slippage during the insertion process. Should a woman desire to utilize the first or second pairs of flat surfaces 52 and 54, or 56 and 58, respectively, she can position her thumb and middle finger on the second section 50. Should the woman desire to utilize the oval-shaped section 48, she can position her thumb and middle finger on the exterior periphery 34 of the first section 48. This unique fingergrip portion 20 thereby provides a variety of ways for a woman to hold the curved tampon applicator 10 in a fashion which feels the most comfortable to her.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. A curved tampon applicator comprising:
   a) a tubular member having an arcuate shape with a centerline formed on an arc having a predetermined radius of curvature, said tubular member having a stepped outer profile with an enlarged portion designed to house a tampon joined to a smaller fingergrip portion, said member having a forward end through which said tampon can be ejected and a rearward end through which a plunger is slidable, said fingergrip portion having a passageway formed therethrough which is sized and configured to receive said plunger and having an exterior periphery;
   b) a first pair of flat surfaces formed on said exterior periphery of said fingergrip portion which are aligned parallel to a plane coincident with a radius forming said arcuate centerline of said member; and
   c) a second pair of flat surfaces formed on said exterior periphery of said fingergrip portion which are aligned perpendicular to said first pair of flat surfaces, said second pair of flat surfaces being shorter in length than said first pair of flat surfaces.

2. A curved tampon applicator comprising:
   a) a tubular member having an arcuate shape with a centerline formed on an arc having a predetermined radius of curvature, said tubular member having a stepped outer profile with an enlarged portion designed to house a tampon joined to a smaller fingergrip portion, said member having a forward end through which said tampon can be ejected and a rearward end through which a plunger is slidable, said fingergrip portion having a passageway formed therethrough which is sized and configured to receive said plunger and having an exterior periphery;
   b) a first pair of flat surfaces formed on said exterior periphery of said fingergrip portion which are aligned parallel to a plane coincident with a radius forming said arcuate centerline of said member;
   c) a second pair of flat surfaces formed on said exterior periphery of said fingergrip portion which are aligned perpendicular to said first pair of flat surfaces, said second pair of flat surfaces being shorter in length than said first pair of flat surfaces; and
   d) a plurality of spaced apart ribs each completely surrounding said exterior surface of said fingergrip portion, at least one of said ribs cooperating with said first and second pairs of flat surfaces to prevent rotation and slippage of said curved tampon applicator during insertion of said tampon into a woman's vagina.

3. The curved tampon applicator of claim 2 wherein said ribs are aligned parallel to one another.

4. The curved tampon applicator of claim 2 wherein said fingergrip portion has a wall which varies in thickness.

5. The curved tampon applicator of claim 4 wherein said wall thickness of said fingergrip portion adjacent to said second pair of flat surfaces is equal to said wall thickness adjacent to said first pair of flat surfaces.

6. The curved tampon applicator of claim 5 wherein said wall adjacent to said first and second pairs of flat surfaces has a thickness of between about 0.6 to 0.7 millimeters.

7. The curved tampon applicator of claim 2 wherein a portion of said fingergrip portion has a generally rectangular cross-sectional configuration.

8. The curved tampon applicator of claim 7 wherein said generally rectangular cross-sectional configuration has rounded corners.

9. The curved tampon applicator of claim 8 wherein said rounded corners have a greater thickness than other portions of said wall.

10. The curved tampon applicator of claim 8 wherein said rounded corners have a wall thickness of between about 0.5 to 1.2 millimeters.

11. A curved tampon applicator comprising:
 a) a tubular member having an arcuate shape with a centerline formed on an arc having a predetermined radius of curvature, said tubular member having a stepped outer profile with an enlarged portion designed to house a tampon joined to a smaller fingergrip portion, said member having a forward end through which said tampon can be ejected and a rearward end through which a plunger is slidable, said plunger designed to engage one end of said tampon and push said tampon out said forward end when said plunger is inserted into said enlarged portion, said fingergrip portion having an oval-shaped passageway formed therethrough which is sized and configured to receive said plunger and having an exterior periphery;
 b) a first pair of flat surfaces formed on said exterior periphery of said fingergrip portion which are aligned parallel to a plane coincident with a radius forming said arcuate centerline of said member;
 c) a second pair of flat surface formed on said exterior periphery of said fingergrip portion which are aligned perpendicular to said first pair of flat surfaces, said second pair of flat surfaces being shorter in length than said first pair of flat surfaces; and
 d) a plurality of spaced apart ribs each completely surrounding said exterior surface of said fingergrip portion, a majority of said ribs cooperating with said first and second pairs of flat surfaces to prevent rotation and slippage of said curved tampon applicator during insertion of said tampon into a woman's vagina.

12. The curved tampon applicator of claim 11 wherein said ribs form a closed loop having a cross-sectional configuration which matches the profile of a portion of said exterior periphery of said fingergrip portion.

13. The curved tampon applicator of claim 11 wherein said fingergrip portion contains five ribs, two of said ribs having a circular cross-sectional configuration.

14. The curved tampon applicator of claim 11 wherein said first and second pairs of flat surfaces extend more than half of the length of said fingergrip portion starting from said rearward end.

15. The curved tampon applicator of claim 11 wherein said first and second pairs of flat surfaces extend a distance along the centerline of said fingergrip portion of between about 8 to 15 millimeters.

16. A curved tampon applicator comprising:
 a) a plunger having an arcuate shape with a centerline formed on an arc having a predetermined radius of curvature, said plunger having an oval-shaped outer configuration;
 b) a tubular member having an arcuate shape with a centerline formed on an arc having a predetermined radius of curvature, said tubular member having a stepped outer profile with an enlarged portion designed to house a catamenial tampon joined to a smaller fingergrip portion, said member having a forward end through which said tampon can be ejected and a rearward end through which said plunger is slidable, said fingergrip portion having an oval-shaped passageway formed therethrough which is sized to receive said plunger and having an exterior periphery, said plunger and tubular member being telescopically engageable and operable to push said tampon out said forward end of said tubular member when said plunger is moved into said member;
 c) a first pair of flat surfaces formed on said exterior periphery of said fingergrip portion which are aligned parallel to a plane coincident with a radius forming said arcuate centerline of said member;
 d) a second pair of flat surface formed on said exterior periphery of said fingergrip portion which are aligned perpendicular to said first pair of flat surfaces, said second pair of flat surfaces being shorter in length than said first pair of flat surfaces; and
 e) a plurality of spaced apart ribs, each completely surrounding said exterior surface of said fingergrip portion, at least one of said ribs cooperating with said first and second pairs of flat surfaces to prevent rotation and slippage of said curved tampon applicator during insertion of said tampon into a woman's vagina.

17. The curved tampon applicator of claim 16 wherein said first pair of flat surfaces extend a distance along the centerline of said fingergrip portion of between about 8 to 15 millimeters.

18. The curved tampon applicator of claim 16 wherein said second pair of flat surfaces extend a distance along the centerline of said fingergrip portion of between about 8 to 15 millimeters.

19. The curved tampon applicator of claim 16 wherein said exterior periphery of said fingergrip portion has a generally rectangular cross-sectional configuration.

20. The curved tampon applicator of claim 16 wherein said exterior periphery of said fingergrip portion has rounded corners, and said rounded corners have a wall thickness greater than adjacent wall portions.

21. The curved tampon applicator of claim 16 wherein said fingergrip portion has a wall which varies in thickness.

* * * * *